US009168338B2

(12) United States Patent
Chen

(10) Patent No.: US 9,168,338 B2
(45) Date of Patent: Oct. 27, 2015

(54) SYRINGE WITH A BLOCKING STRUCTURE

(71) Applicant: Cho-Ying Chen, Taichung (TW)

(72) Inventor: Cho-Ying Chen, Taichung (TW)

(73) Assignees: Hsiao I Fan, Taichung (TW); Hshin Chung Lee, Taoyuan (TW)

( * ) Notice: Subject to any disclaimer, the term of this patent is extended or adjusted under 35 U.S.C. 154(b) by 281 days.

(21) Appl. No.: 13/872,256

(22) Filed: Apr. 29, 2013

(65) Prior Publication Data

US 2013/0338605 A1 Dec. 19, 2013

(30) Foreign Application Priority Data

Jun. 15, 2012 (TW) .............................. 101121549 A

(51) Int. Cl.
*A61M 5/00* (2006.01)
*A61M 5/315* (2006.01)
*A61M 5/32* (2006.01)

(52) U.S. Cl.
CPC ........... *A61M 5/31501* (2013.01); *A61M 5/322* (2013.01); *A61M 5/3234* (2013.01); *A61M 2005/3235* (2013.01); *A61M 2005/3236* (2013.01)

(58) Field of Classification Search
CPC ..................... A61M 5/322; A61M 2005/3235; A61M 5/3234; A61M 2005/3236
See application file for complete search history.

(56) References Cited

U.S. PATENT DOCUMENTS

| 5,370,620 | A | * | 12/1994 | Shonfeld | 604/110 |
| 7,179,243 | B2 | * | 2/2007 | Chen | 604/110 |
| 2007/0244443 | A1 | * | 10/2007 | Chen | 604/195 |
| 2010/0185147 | A1 | * | 7/2010 | Chen | 604/110 |
| 2013/0116619 | A1 | * | 5/2013 | Chen | 604/110 |

* cited by examiner

*Primary Examiner* — Aarti B Berdichevsky
(74) *Attorney, Agent, or Firm* — Rosenberg, Klein & Lee

(57) ABSTRACT

A syringe with a blocking structure, and the structure includes a one-way engagement unit having a propping portion, a flange extended outwardly from a rod and abutted with a cylindrical body, and a flexible bracket extended outwardly from the rod and isolated from the propping portion, and the flexible bracket has an external diameter greater than the propping portion. When the rod is moved forward with respect to the cylindrical body to pass through the flange, the flange abuts the flexible bracket to tilt backward. When the rod is moved backward with respect to the cylindrical body, the flange abuts the flexible bracket to tilt the flexible bracket forward, and the propping portion blocks the flexible bracket.

10 Claims, 14 Drawing Sheets

SYRINGE WITH A BLOCKING STRUCTURE

FIELD OF THE INVENTION

The present invention relates to a syringe, and more particularly to the syringe with a blocking structure.

BACKGROUND OF THE INVENTION

With reference to FIG. 1 for an improved disposable safety syringe structure (as disclosed in R.O.C. Utility Model No. M360049), the improved disposable safety syringe structure comprises a cylindrical body 11, a needle seat 12, and a plunger 3, wherein the plunger 3 has a piston head 131, and a latch edge 133, and the cylindrical body 11 has a flange 16 and two positioning bases 111, and each of the positioning bases 111 has an engagement slot 112, and the needle seat 12 has a fitting section 121 disposed at a front end of the needle seat 12 for combining an injection needle 14 and an elastic inverted hook plate 122 disposed at a rear end of the needle seat 12, and the needle seat 12 has a plurality of convex column engagement members 123 disposed at a front end of the needle seat 12. When the needle seat 12 is assembled into the cylindrical body 11, the convex column engagement members 123 are engaged with the engagement slots 112 of the positioning bases 111 of the cylindrical body 11 respectively. The piston head 131 has a piston plate 15, and the piston head 131 has a circular flange 132 disposed at a front end of the piston head 131. After medicine is injected, the piston head 131 can be forced to plug into the needle seat 12, and the circular flange 132 of the piston head 131 is hooked to the inverted hook plate 122 of the needle seat 12, so that the piston head 131 and the needle seat 12 are coupled integrally as a whole, and the piston head 131 drives the convex column engagement member 123 of the needle seat 12 to be separated from the engagement slot 112 of the positioning base 111 of the cylindrical body 11, and the piston head 131 of the plunger 3 is retracted to drive the needle seat 12 and the injection needle 14 to be retracted into the cylindrical body 11 to achieve the effects of hiding the needle seat 12 and the injection needle 14 and preventing injuries or accidents.

Although the foregoing improved disposable safety syringe structure can achieve the effect of preventing accidents or injuries effectively, the disposable safety syringe structure just can prevent the plunger 3 from detaching from the cylindrical body 11 by interfering the piston plate 15, the latch edge 133 and the flange 16. However, if the design of the relation between the latch edge 133 and the flange 16 is too loose, then when the injection needle 14 extends into the cylindrical body 11, the injection needle 14 may be retracted to the outside and may cause accidents. If the design of the relation between the latch edge 133 and the flange 16 is too tightly, then when the plunger 3 is installed into the cylindrical body 11 and pushed forward, the plunger will not be pushed easily. Therefore, the conventional structure of the latch edge 133 and the flange 16 requires further improvements.

SUMMARY OF THE INVENTION

In view of the aforementioned drawbacks of the prior art, it is a primary objective of the present invention to provide a syringe with a blocking structure to overcome the aforementioned drawbacks.

To achieve the aforementioned objective, the present invention provides a syringe comprising a cylindrical body, a rod and a one-way engagement unit, and the cylindrical body includes a flange, and the one-way engagement unit includes a propping portion and a flexible bracket. The propping portion is extended outwardly from the rod and can abut the flange, and the flexible bracket is extended outwardly from the rod and isolated from the propping portion. The flexible bracket has an external diameter greater than the external diameter of the propping portion, and the rod is pushed forward with respect to the cylindrical body, so that when the propping portion and the flexible bracket pass through the flange, the flange abuts the flexible bracket to tilt backward, and when the rod is pushed backward with respect to the cylindrical body, the flange abuts the flexible bracket to tilt the flexible bracket forward, so that the propping portion blocks the flexible bracket.

One of the effects of the present invention is to abut the one-way engagement unit against the flange of the cylindrical body during the process of retreating from the cylindrical body, such that the propping portion blocks the tilted flexible bracket to define a blocking effect and produce the one-way engagement effect.

Another effect of the present invention is to abut the head holder section of the needle seat against the circular body in the barrel, such that when the head holder section of the needle seat is warped by the barrel inverted hook plate, the head holder section of the needle seat is blocked in the barrel and stably positioned in the cylindrical body to assure the function of the seal ring for preventing leakage.

DESCRIPTION OF THE PREFERRED EMBODIMENTS

The technical characteristics, contents, advantages and effects of the present invention will be apparent with the detailed description of a preferred embodiment accompanied with related drawings as follows. It is noteworthy to point out that the terms including "front" and "rear" are used for relative positions and as a reference for normal positioning.

Figure 1:
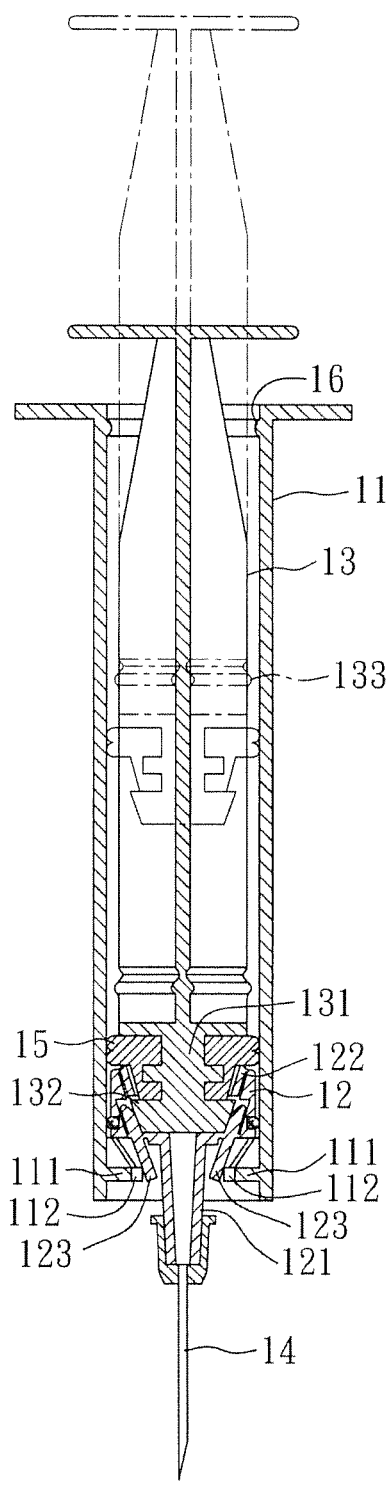
FIG. 1 is a cross-sectional view of a conventional disposable safety syringe structure.
Figure 2:
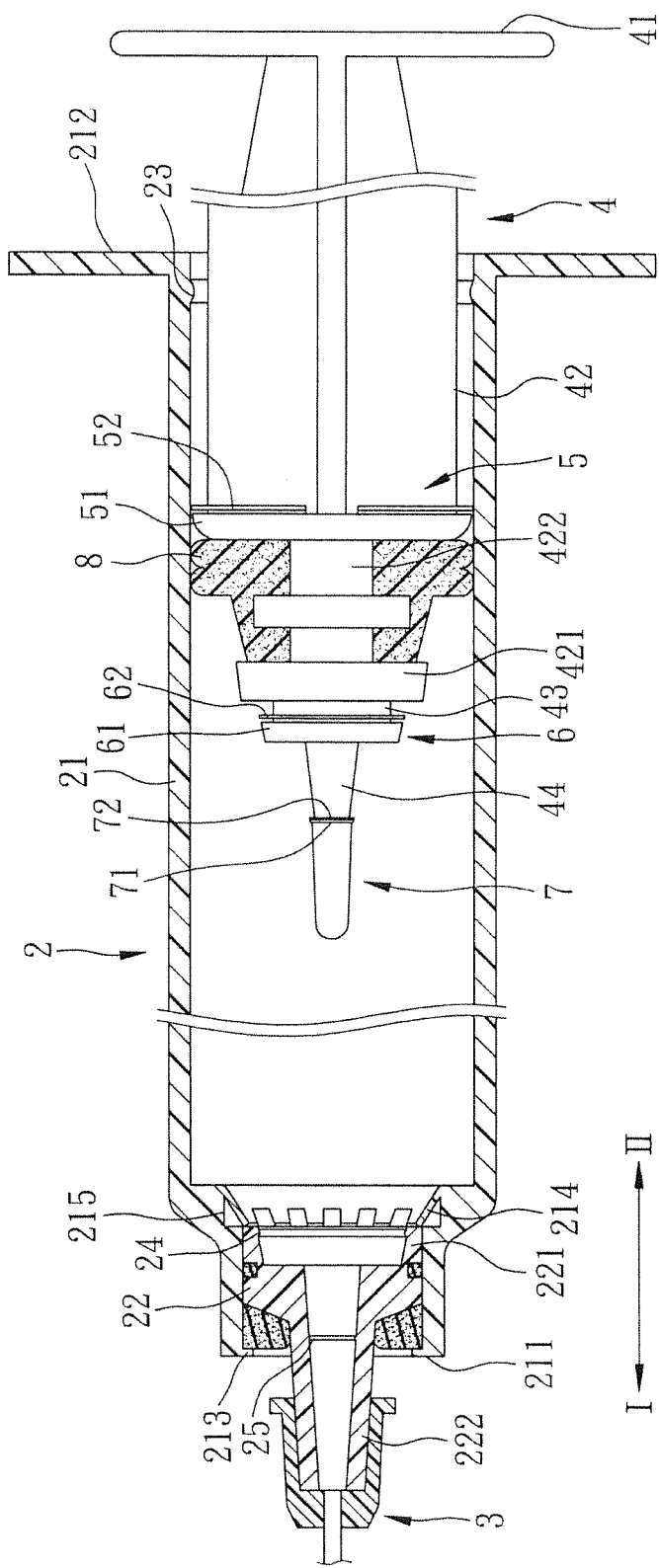
FIG. 2 is a cross-sectional view of a syringe with a blocking structure and a cylindrical body in accordance with a first preferred embodiment of the present invention.
Figure 3:
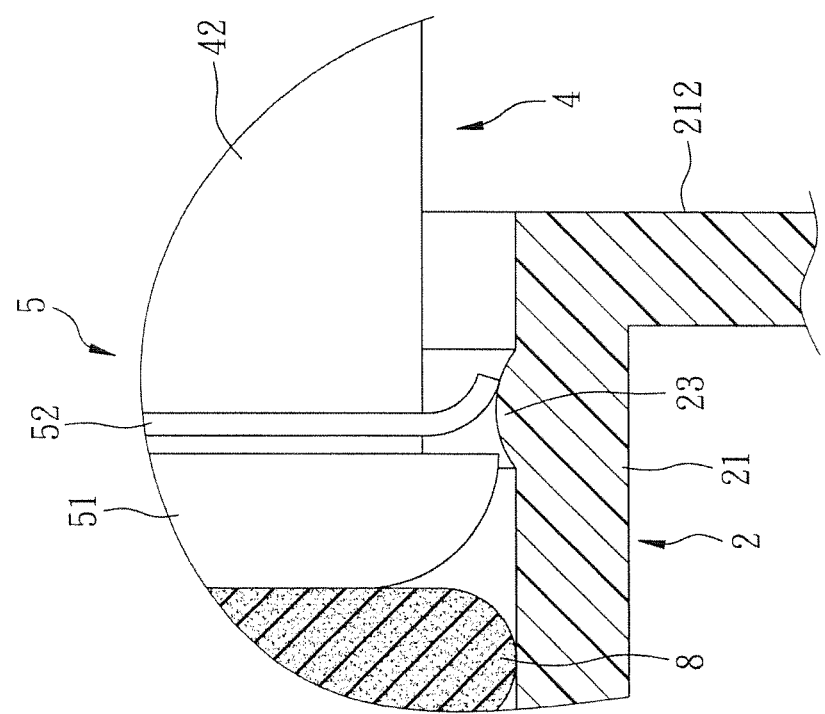
FIG. 3 is schematic partial view of a flexible bracket of a one-way engagement unit being pushed forward to abut one of the flanges and tilted in accordance with the first preferred embodiment of the present invention.

With reference to FIGS. 2 and 3 for a syringe with a blocking structure in accordance with a preferred embodiment of the present invention, the syringe comprises a cylindrical body 2, a rod 4 and three one-way first, second and third engagement units 5, 6, 7, respectively.

In FIG. 2, the cylindrical body 2 of the present invention comprises a barrel 21, a needle seat 22 combined with the barrel 21, and three first, second and third flanges 23, 24, 25, respectively. The barrel 21 comprises a front end 211, a rear end 212 opposite to the front end 211, a front positioning base 213 formed at the front end 211 for positioning the needle seat 22, a barrel inverted hook plate 214 formed on an internal surface of the barrel 21 and extended towards the front end 211, and a groove 215 capable of accommodating the barrel inverted hook plate 214. The barrel inverted hook plate 214 is in a circular shape and has an elastic restoring force for abutting the needle seat 22. The needle seat 22 comprises a head holder section 221 and a fitting section 222 extended from the head holder section 221 for combining an injection needle 3. The first, second and third flanges 23, 24, 25 are formed around the barrel 21 and proximate to an internal surface of the rear end 212, an internal surface of the head holder section 221, and an internal surface of the fitting section 222 respectively.

The rod 4 comprises a pushing end 41, a rod body section 42 proximate to the pushing end 41, an engagement section 43 extended from the rod body section 42 in a direction opposite to the pushing end 41, and a top rod section 44 extended from the engagement section 43 in a direction opposite to the pushing end 41. The rod body section 42 comprises a circular flange 421 formed at a front end of the rod body section 42 and a piston seat 422 isolated from the circular flange 421 and disposed opposite to the circular flange 421 and proximate to the pushing end 41, wherein the piston seat 422 is provided for connecting a piston plate 8 used for preventing a leakage of liquid medicine. The engagement section 43 can accommodate the head holder section 221 of the needle seat 22. The top rod section 44 can accommodate the fitting section 222 of the needle seat 22.

Figure 7:
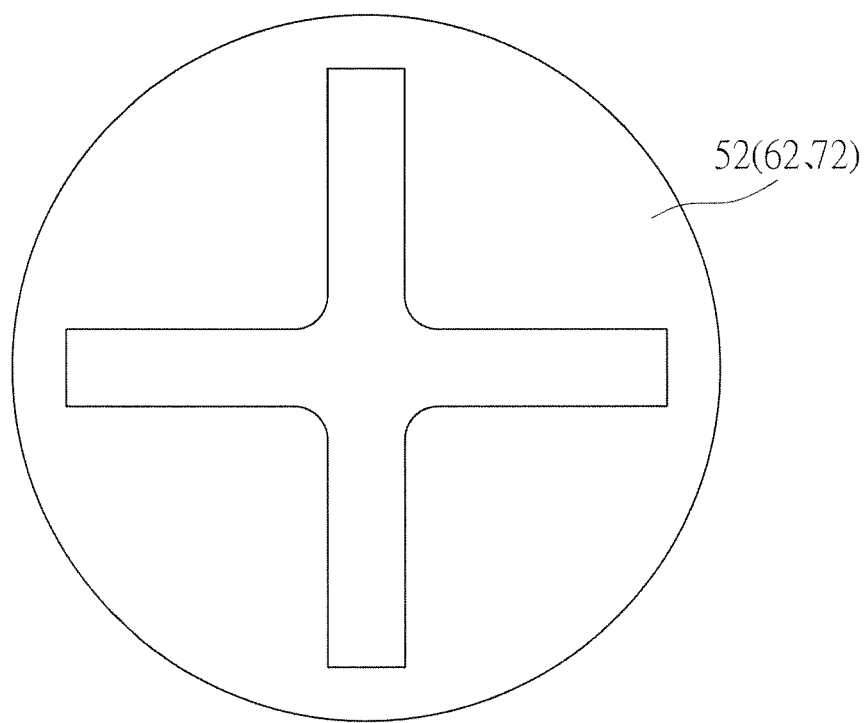
FIG. 7 is a schematic view of a circular structure of a flexible bracket in accordance with the first preferred embodiment of the present invention.

Each of the first, second and third one-way engagement units 5, 6, 7 comprises a first, second and third circular propping portion 51, 61, 71, respectively, disposed at a position away from the pushing end 41 of the rod 4, and a first, second and third circular flexible bracket 52, 62, 72, respectively, disposed at a position opposite to the first, second and third propping portions 51, 61, 71 and proximate to the pushing end 41 of the rod 4 (as shown in FIG. 7). The first, second and third propping portions 51, 61, 71 of the first, second and third one-way engagement units 5, 6, 7 are extended from the rod body section 42, the engagement section 43, and the top rod section 44 towards their external diameters respectively, and the first, second and third flexible brackets 52, 62, 72 of the first, second and third one-way engagement units 5, 6, 7 are extended from the rod body section 42, the engagement section 43, and the top rod section 44 to their external diameters and isolated from the first, second and third propping portions 51, 61, 71 respectively.

It is noteworthy that the rod 4 has an external diameter smaller than the internal diameter of the cylindrical body 2, and the barrel 21 of the cylindrical body 2 has an internal diameter greater than the external diameter of the first, second and third flexible brackets 52, 62, 72, and the first, second and third flexible brackets 52, 62, 72 have an external diameter greater than the external diameters of the first, second and third propping portions 51, 61, 71 respectively, and the first, second and third propping portions 51, 61, 71 have the external diameters equal to the internal diameters of the first, second and third flanges 23, 24, 25 respectively, so that when the rod 4 is pushed towards a positive axis direction I with respect to the cylindrical body 2 to pass the first propping portion 51 and the first flexible bracket 52 through the first flange 23, the first propping portion 51 can abut the first flange 23, and the first flange 23 abuts the first flexible bracket 52 to tilt the first flexible bracket 52 towards a negative axis direction II and pass through the first flange 23. It is noteworthy that the first flexible bracket 52 has an elastic restoring force, so that when the first flexible bracket 52 is passed through the first flange 23, the elastic restoring force can restore the first flexible bracket 52 to its original shape.

Figure 4:
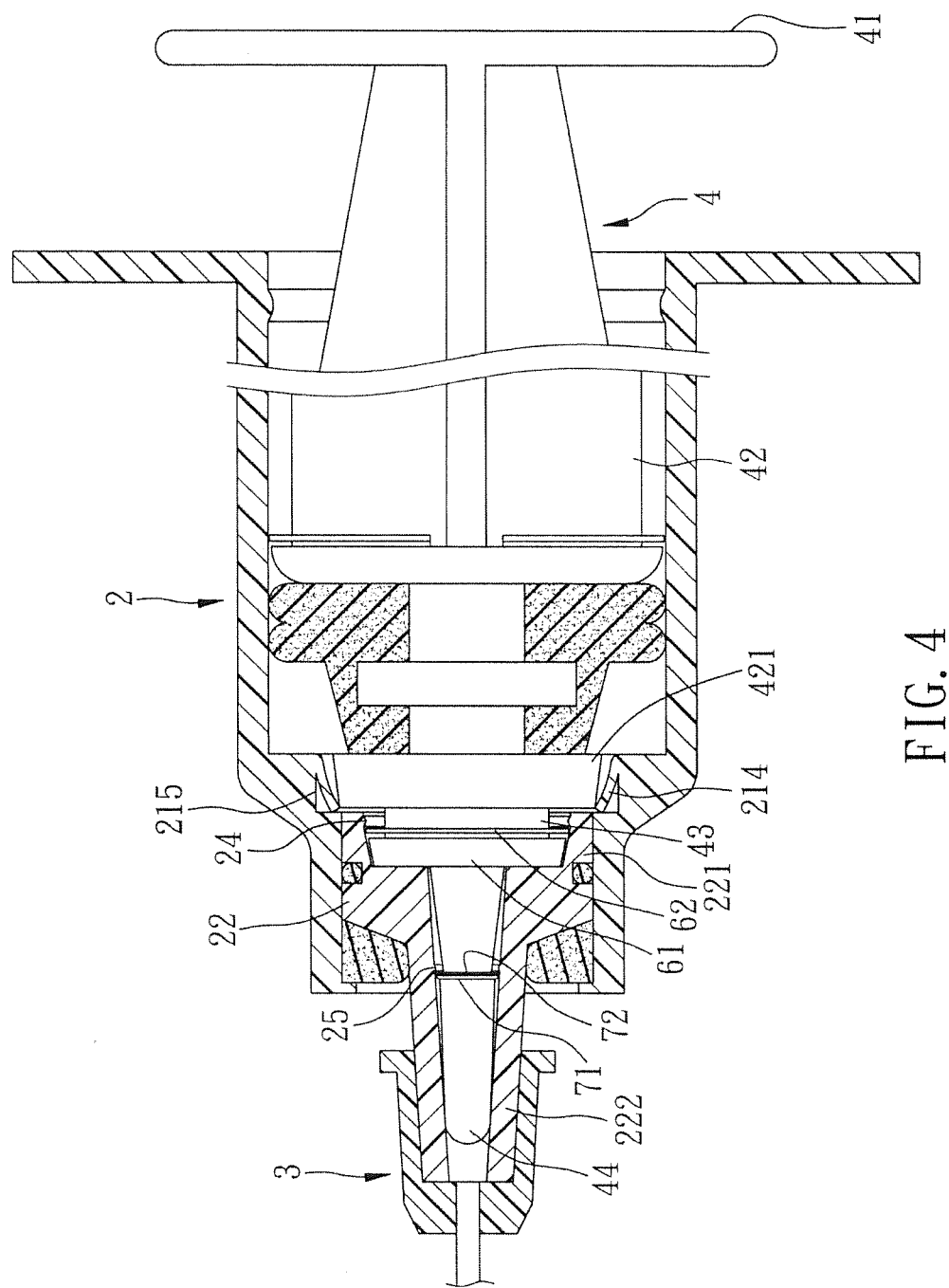
FIG. 4 is another cross-sectional view of the first preferred embodiment with the cylindrical body, and a rod of the first preferred embodiment being engaged with a needle seat and a fitting section of the cylindrical body.
Figure 5:
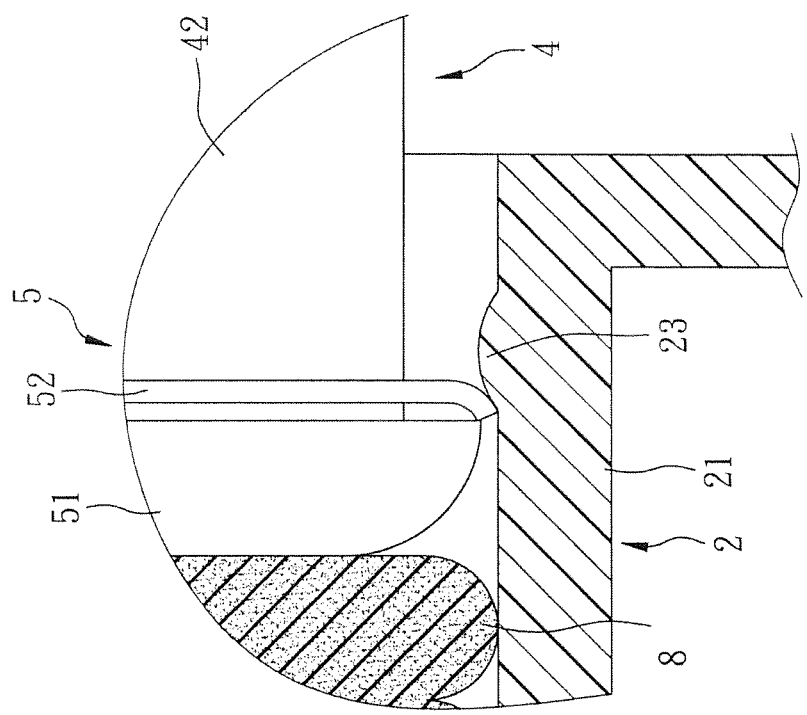
FIG. 5 is a schematic partial view of a flexible bracket of a one-way engagement unit being pushed backward to abut one of the flanges and tilted in accordance with the first preferred embodiment of the present invention.

In FIGS. 2, 4 and 5, after a user completes the injection, the user can continue pushing the pushing end 41 of the rod 4 in the positive axis direction I to force the circular flange 421 of the rod body section 42 to retract the barrel inverted hook plate 214 into the groove 215, and the engagement section 43 is accommodated in the head holder section 221 of the needle seat 22, and the top rod section 44 is accommodated in the fitting section 222 of the needle seat 22. When the second and third propping portions 61, 71 and the second and third flexible brackets 62, 72 are passed through the second and third flanges 24, 25, the second and third propping portions 61, 71 of the second and third one-way engagement units 6, 7 respectively formed on the engagement section 43 and the top rod section 44 can abut the second and third flanges 24, 25 on the internal surface of the head holder section 221 and the internal surface of the fitting section 222 respectively, and the second and third flanges 24, 25 abut the second and third flexible brackets 62, 72 in the negative axis direction II by force to pass through the second and third flanges 24, 25. It is noteworthy that the second and third flexible brackets 62, 72 have elastic restoring force, so that when the second and third flexible brackets 62, 72 are passed through the second and third flanges 24, 25, the second and third flexible brackets 62, 72 can restore their original shape. In addition, the first, second and third propping portions 51, 61, 71 are rigid, and the first, second and third flexible brackets 52, 62, 72 are bias valve plates, so that when the rod 4 is moved in the positive axis direction I opposite to the cylindrical body 4, the first, second and third flexible brackets 52, 62, 72 are not supported, so that they are tilted and passed through the first, second and third flanges 23, 24, 25.

When a user pulls the rod 4 to move in the negative axis direction II with respect to the cylindrical body 2, the second and third flanges 24, 25 abut the second and third flexible brackets 62, 72 of the second and third one-way engagement units 6, 7 to tilt towards the positive axis direction I, the second and third propping portions 61, 71 block the second and third flexible brackets 62, 72 respectively to produce a one-way engagement effect, so that the needle seat 22 can be securely combined with the rod 4, and the needle seat 22 and the injection needle 3 together with the rod 4 are retracted into the barrel 21.

Figure 6:
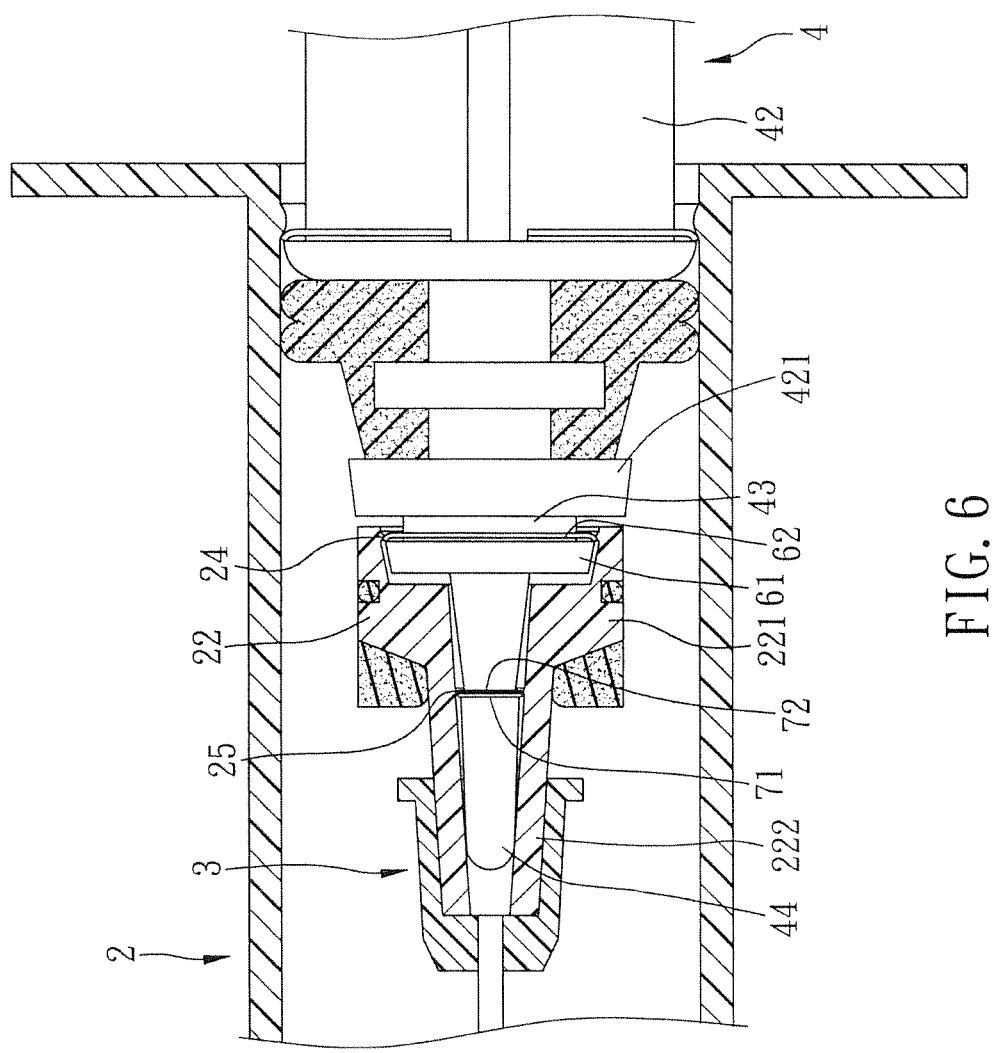
FIG. 6 is another cross-sectional view of the first preferred embodiment with the cylindrical body of the present invention.

In FIGS. 2, 5 and 6, when the rod 4 continues to retract from the cylindrical body 2 in the negative axis direction II, and the first flange 23 formed on the internal surface of the barrel 21 abuts the first flexible bracket 52 of the rod body section 42 to tilt in the positive axis direction I, the first propping portion 51 blocks the first flexible bracket 52 to produce a one-way engagement effect and prevent the rod 4 together with the needle seat 22 and the injection needle 3 from being separately completely from the barrel 21, so as to prevent accidents or injuries. It is noteworthy that when the first, second and third flexible brackets 52, 62, 72 tilts in the positive axis direction I, the first, second and third propping portions 51, 61, 71 blocks the first, second and third flexible brackets 52, 62, 72 and stop them from tilting further or passing through the first, second and third flanges 23, 24, 25. The angles of the first, second and third propping portions 51, 61, 71 and the gap of the first, second and third flexible brackets 52, 62, 72 are designed so that the first, second and third flexible brackets 52, 62, 72 are tilted in the positive axis direction I with an angle smaller than the tilting angle towards the negative axis direction 11.

It is noteworthy that the syringe with a blocking structure of this preferred embodiment of the present invention comprises three one-way engagement units 5, 6, 7, and the syringe with a blocking structure comprises the one-way engagement unit 5, 6, 7 formed at any two of the rod body section 42, the engagement section 43 and the top rod section 44, or the syringe with a blocking structure just comprises one-way engagement unit 5, 6, 7 formed at one of the rod body section 42, the engagement section 43 and the top rod section 44 to produce a one-way engagement effect.

It is noteworthy that the way of securing the barrel 21 with the needle seat 22 includes but not limited to using the barrel inverted hook plate 214 to abut the needle seat 22, or using a general engagement structure for the connection. However, these are prior arts easily accomplished by persons having ordinary skill in the art, so that they will not be described in details.

In summation, the syringe with a blocking structure of the present invention has the following effects and advantages to achieve the objectives of the present invention:

1. When the flanges 23, 24, 25 abut the flexible brackets 52, 62, 72 of the one-way engagement units 5, 6, 7 to tilt in the positive axis direction I, the abutting portions 51, 61, 71 block the flexible brackets 52, 62, 72 to produce a one-way engagement effect.

2. The one-way engagement units 5, 6, 7 can be formed at positions on at least one of the rod body section 42, the engagement section 43 and the top rod section 44 to produce different one-way engagement effects.

Figure 8:
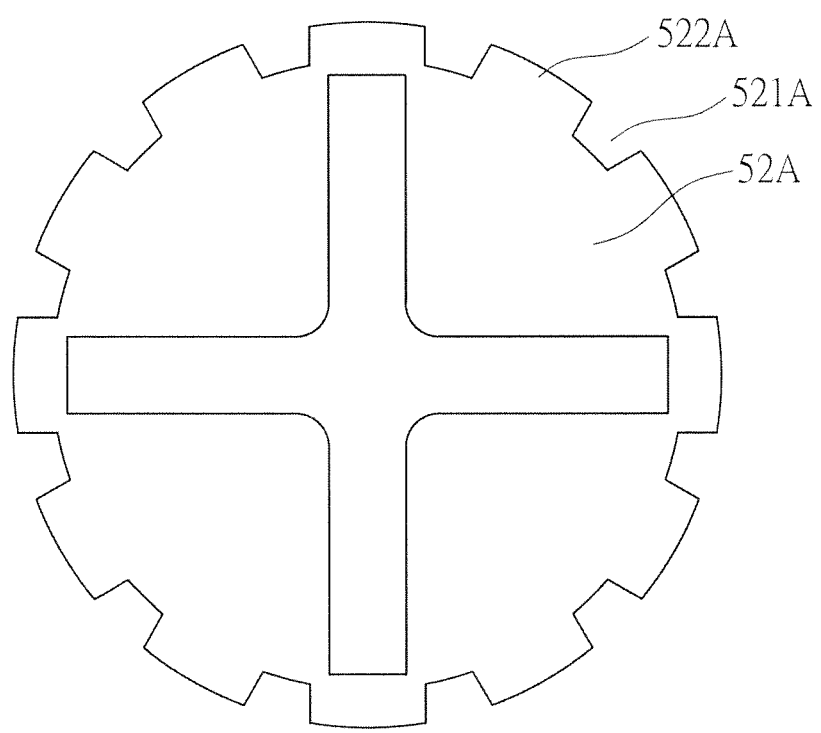
FIG. 8 is a schematic view of a circular structure of a flexible bracket having a plurality of hollow portions and serrated portions disposed around the periphery of the flexible bracket in accordance with a second preferred embodiment of the present invention.

Of course, the present invention may have many other embodiments with a slight difference with each other. With reference to FIG. 8 for a second preferred embodiment of the present invention which has another structural form of the flexible brackets 52, 62, 72 of the first preferred embodiment, the difference between the flexible bracket 52A of this preferred embodiment and the flexible bracket 52 of the first preferred embodiment resides on that the flexible bracket 52A has a plurality hollow portions 521A and serrated portions 522A arranged alternately with one another and disposed around the flexible bracket 52A to constitute a star gear structure, so as to achieve the same one-way engagement effect as the flexible bracket 52 of the first preferred embodiment does. In addition, the flexible brackets 62, 72 of the first preferred embodiment can be changed to this structure, too.

Figure 9:
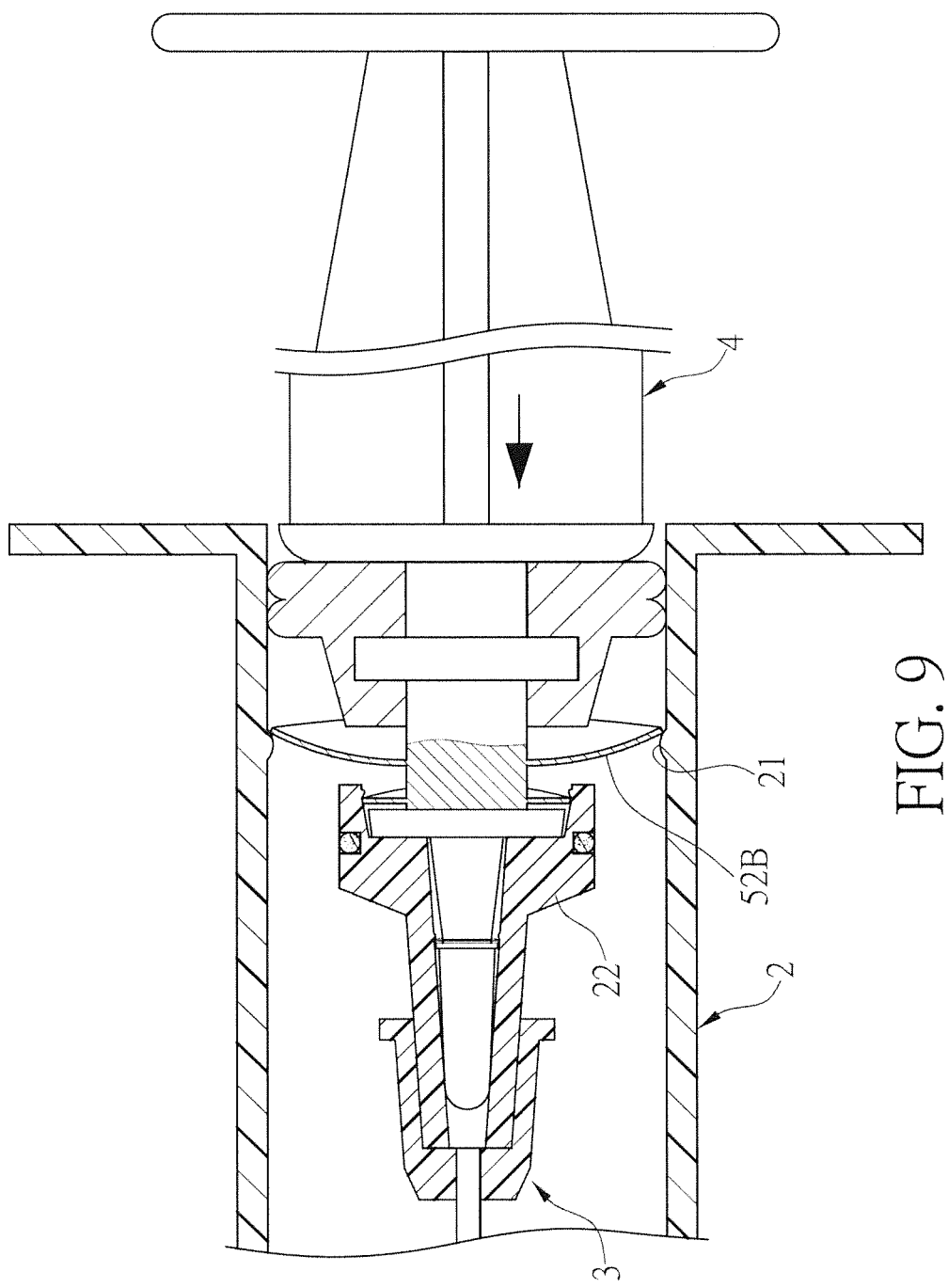
FIG. 9 is a schematic view of an arc-shaped flexible bracket bent with a fingernail shape along the bending direction into a cylindrical body in accordance with a third preferred embodiment of the present invention.
Figure 10:
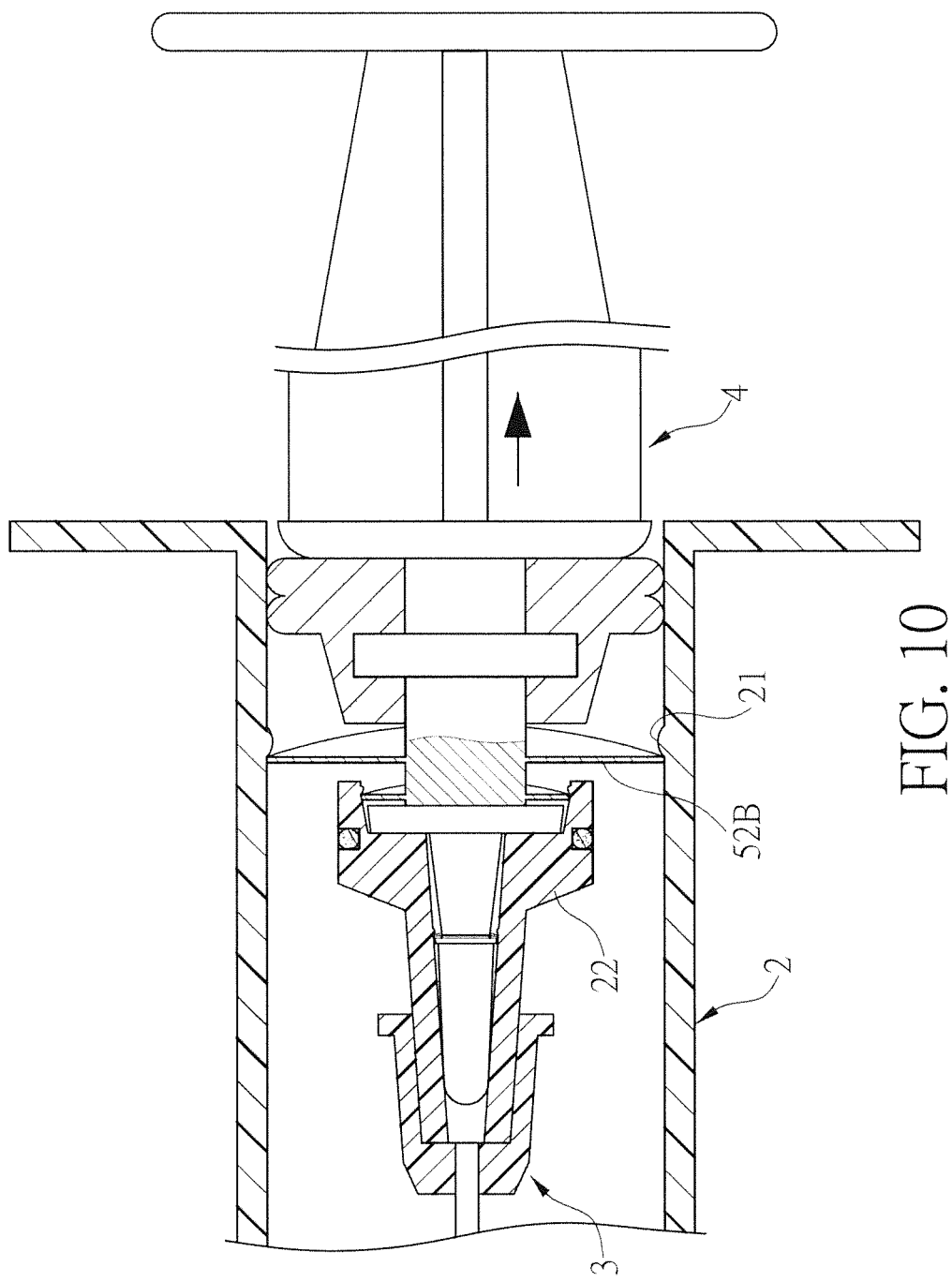
FIG. 10 is a schematic view of an arc-shaped flexible bracket bent with a fingernail shape and being pulled backward with a rod and blocked by a flange in accordance with a third preferred embodiment of the present invention.

With reference to FIGS. 9 and 10 for the third preferred embodiment of the present invention, the flexible brackets of this preferred embodiments are other structures of the flexible bracket 52, 62, 72 of the first preferred embodiment, and the difference of the flexible bracket 52B of this preferred embodiment and the flexible brackets 52, 62, 72 of the first preferred embodiment resides on that the flexible bracket 52B is a bracket having a specific hardness and bent into a fingernail shape. When the rod 4 is pushed forward with respect to the cylindrical body 2 (as shown in FIG. 9), the rod 4 enters along the bending direction of the flexible bracket 52B into the cylindrical body 2. When the rod 4 is pushed backward with respect to the cylindrical body 2, the flexible bracket 52B with a specific hardness is blocked by the flange 21 directly (as shown in FIG. 10) to produce the same one-way engagement effect.

Figure 11:
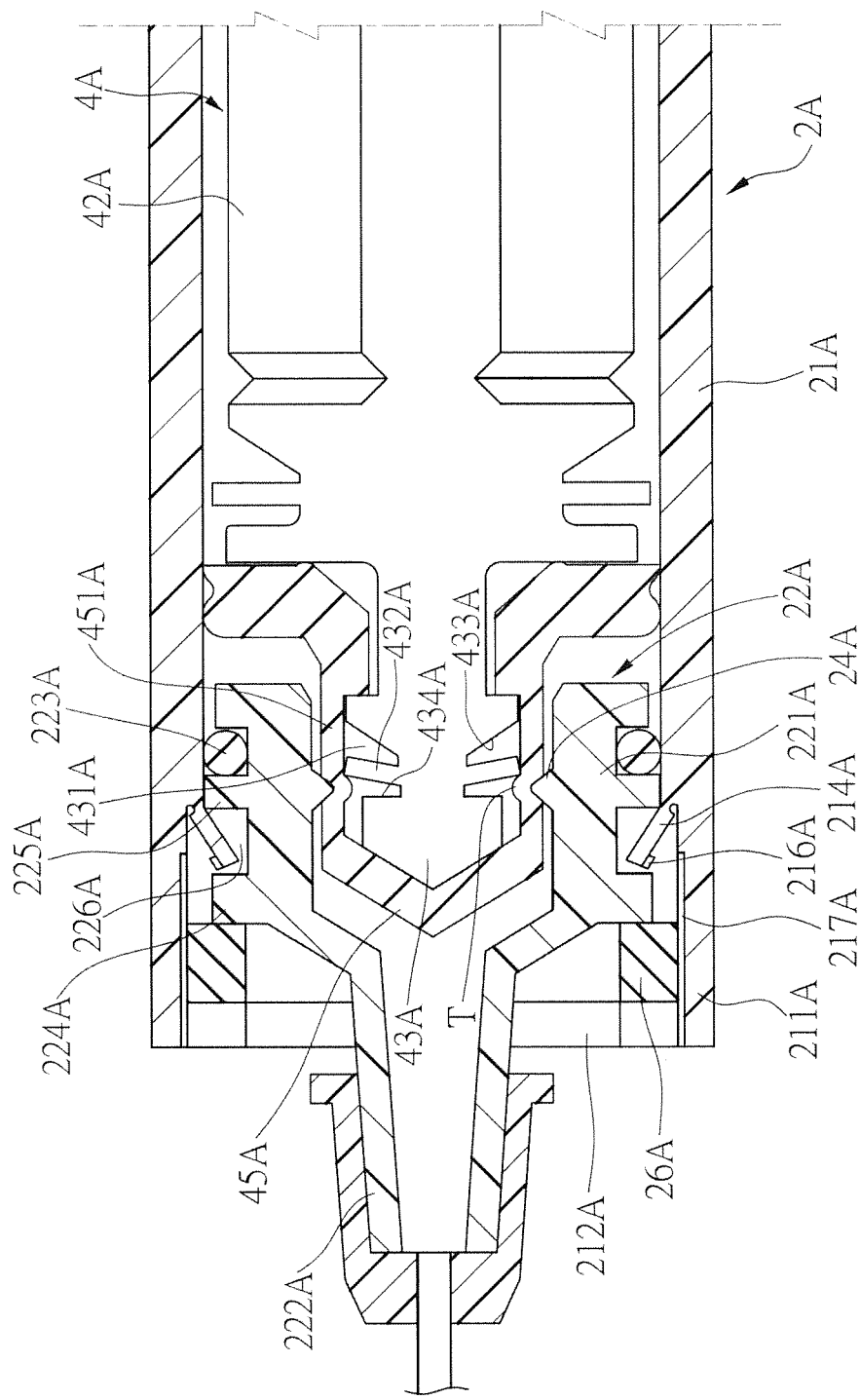
FIG. 11 is a cross-sectional view of a fourth preferred embodiment of the present invention.

With reference to FIGS. 11 to 14 for the fourth preferred embodiment of the present invention, the fourth preferred embodiment as shown in FIG. 11 comprises a cylindrical body 2A and a rod 4A, and the cylindrical body 2A comprises a barrel 21A and a needle seat 22A combined with the barrel 21A, and the barrel 21A has a through hole 212A formed at a front end 211A of the barrel 21A, and the needle seat 22A has a flange 24A formed at a middle position of an internal surface of the needle seat 22A.

In this preferred embodiment, the rod 4A comprises a rod body section 42A, an engagement section 43A extended from the rod body section 42A and accommodated in the needle seat 22A, and a hollow cork cap 45A covered onto the engagement section 43A and plugged into the needle seat 22A, wherein the engagement section 43A has a circular groove 431A and a flexible bracket 432A horizontally extended from the circular groove 431A, and the flange 24A has an internal diameter slightly greater than the external diameter of the flexible bracket 432A, and the periphery 451A of the cork cap 45A has a thickness slightly smaller than the difference between the internal diameter of the flange 24A and the external diameter of the flexible bracket 432A, such that the periphery 451A of the cork cap 45A is protruded into the circular groove 431A by the flange 24A (which defines the protrusion T), and the protrusion T has an internal diameter smaller than the external diameter of the flexible bracket 432A, and the circular groove 431A has a bevel 433A extended slantingly backward from a groove wall at the rear of the flexible bracket 432A, and the circular groove 431A has a plane 434A extended horizontally from the groove wall at the front of the flexible bracket 432A.

In this preferred embodiment, the barrel 21A has a plurality of dovetail grooves 217A uniformly formed at an end of the through hole 212A, and each dovetail groove 217A is axially passed from the barrel 21A into an end of the through hole 212A, and the barrel 21A has a barrel inverted hook plate 214A disposed deeply in each dovetail groove 217A and on an internal side of the dovetail groove 217A, and each barrel inverted hook plate 214A is extended in a direction towards the through hole 212A and tilted slightly downward into the barrel 21A, and each barrel inverted hook plate 214A has a dovetail member 216A disposed at an end of the barrel inverted hook plate 214A and installed in the corresponding dovetail groove 217A.

In this preferred embodiment, a circular body 26A with a square cross section and a specific compressibility is disposed in the barrel 21A and at the bottom of an end of the through hole 212A.

In the needle seat 22A of this preferred embodiment, a head holder section 221A and a fitting section 222A are disposed at an end of the through hole 212A of the barrel 21A, and the periphery of the head holder section 221A has a first circular portion 224A and a second circular portion 225A, and a circular groove 226A is formed between the first circular portion 224A and the second circular portion 225A, and the front edge of the first circular portion 224A abuts the circular body 26A, and when the barrel inverted hook plate 214A is warped, it is extended into the circular groove 226A and blocked by the rear edge of the first circular portion 224A, and the periphery of the second circular portion 225A can push away the barrel inverted hook plate 214A to drive the dovetail member 216A into the dovetail groove 217A, and the head holder section 221A disposed at the rear of the second circular portion 225A abuts a seal ring 223A of the barrel 21A, and the fitting section 222A is extended from the head holder section 221A and out from the through hole 212A.

Figure 12:
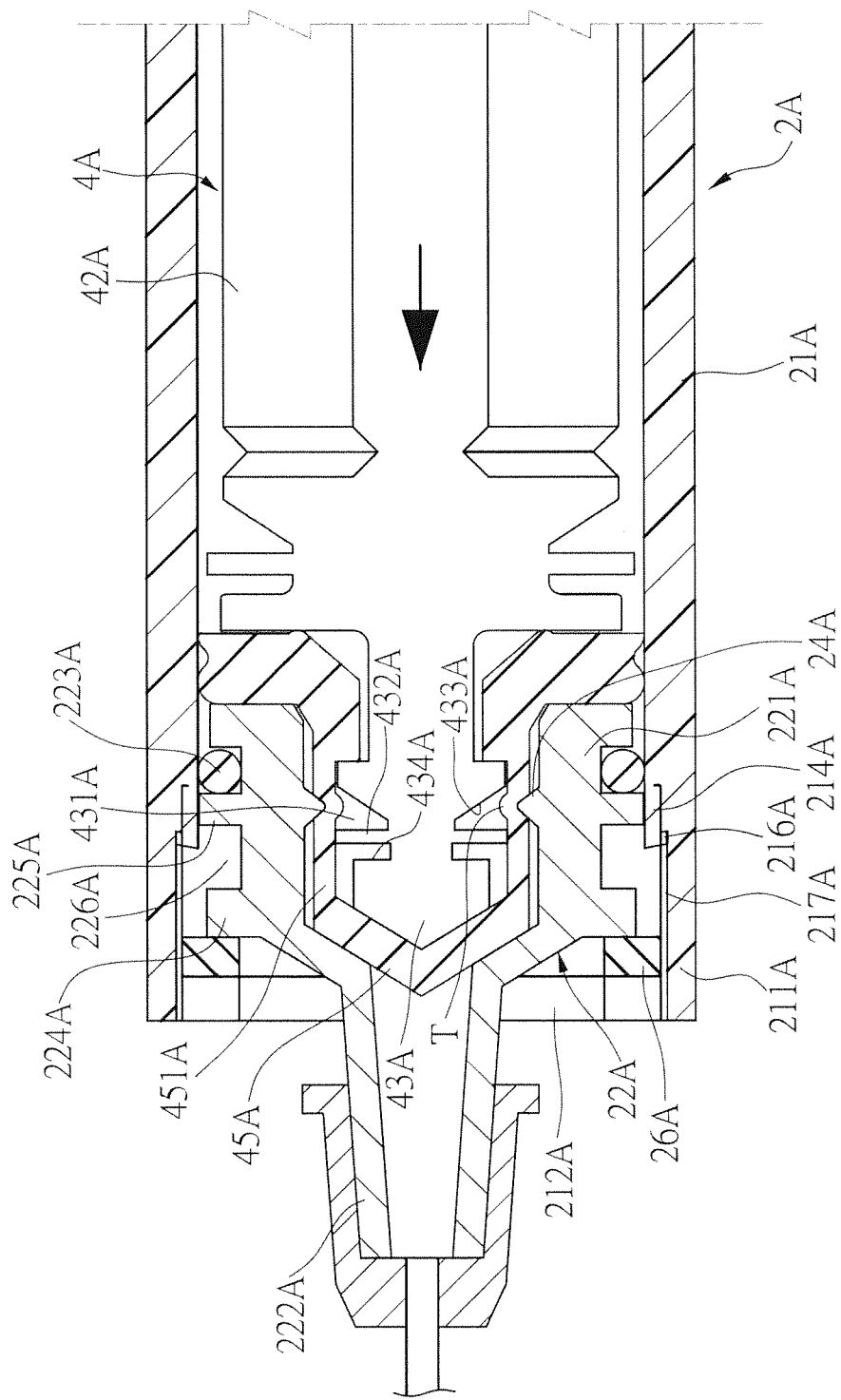
FIG. 12 is a schematic view of an engagement portion combined with a head holder section of a needle seat in accordance with a fourth preferred embodiment of the present invention.

In FIG. 12, when the cork cap 45A together with the engagement section 43A are pushed forward and plugged into the needle seat 22A, and the flexible bracket 432A is moved forward at the rear of the protrusion T, the flexible bracket 432A is pushed by the protrusion T to tilt backwardly towards the bevel 433A, so that the flexible bracket 432A can pass through the protrusion T, and the flexible bracket 432A can resume its horizontal position after passing through the protrusion T.

Figure 13:
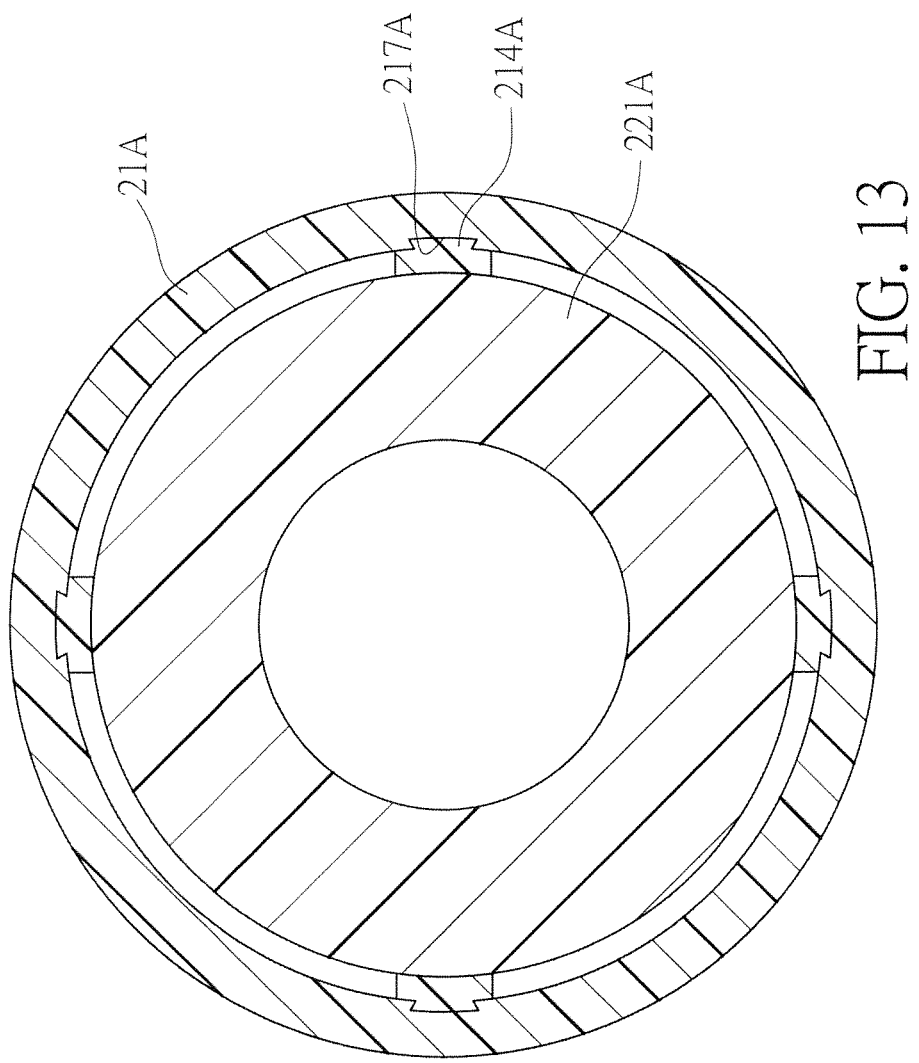
FIG. 13 is a schematic view of a barrel inverted hook plate engaged into a dovetail groove of a barrel by a dovetail member in accordance with the fourth preferred embodiment of the present invention.

In FIGS. 12 and 13, when the cork cap 45A together with the engagement section 43A are pushed forward in a direction towards the needle seat 22A, the head holder section 221A of the needle seat 22A abutted by the cork cap 45A is moved forward, so that the barrel inverted hook plate 214A originally extended from the front end of the barrel 21A front end 211A is abutted and moved forwardly by the second circular portion 225A of the head holder section 221A, so that the barrel inverted hook plate 214A is pushed away and expanded outwardly. Now, the dovetail member 216A at an external side of the barrel inverted hook plate 214A is expanded along the barrel inverted hook plate 214A and engaged into the dovetail groove 217A of the barrel 21A, so that after the barrel inverted hook plate 214A is attached to the barrel 21A for positioning, the head holder section 221A of the needle seat 22A is retracted and separated.

Figure 14:
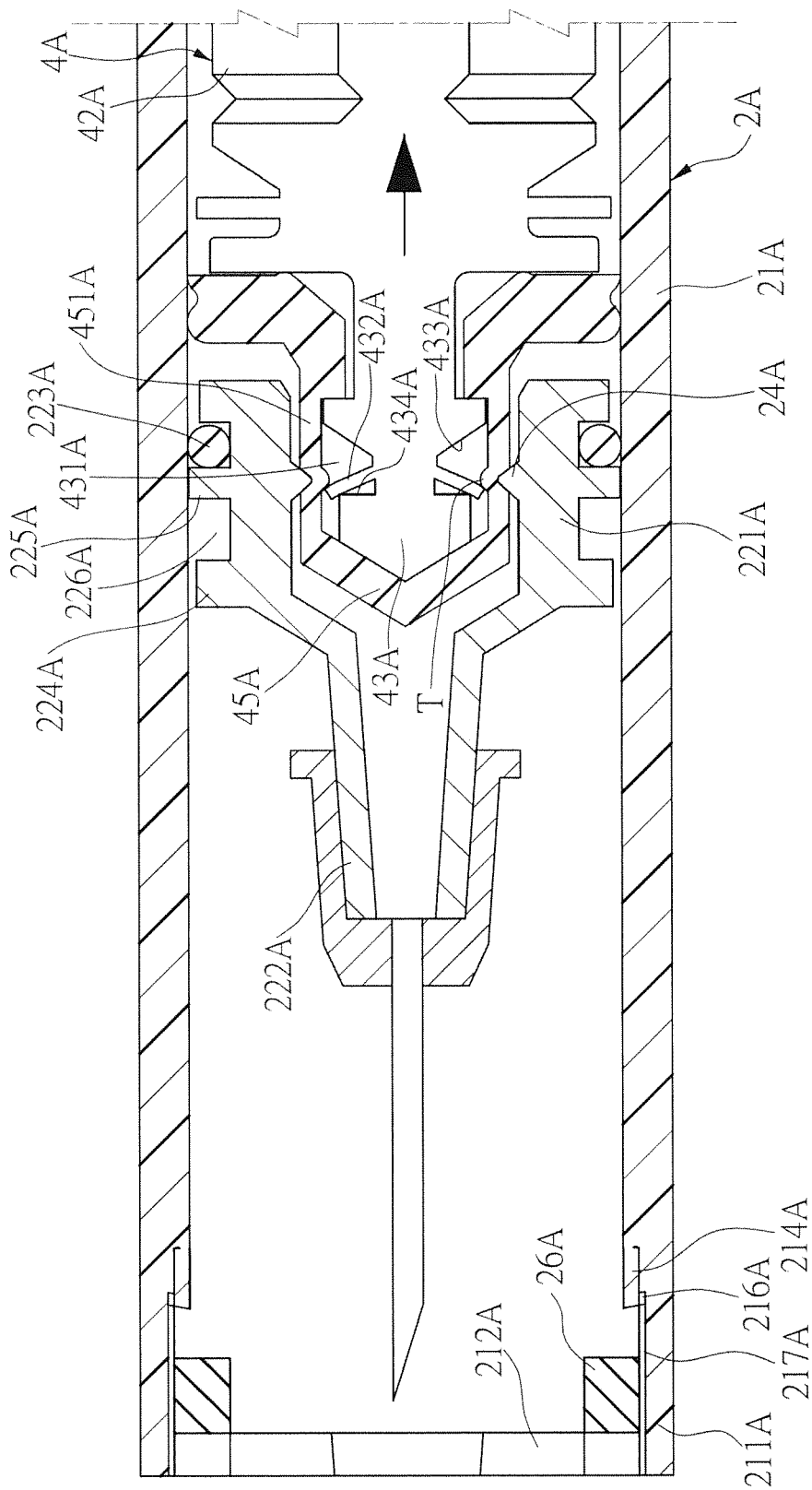
FIG. 14 is a schematic view of the motion of a needle seat being pulled together with a rod into a barrel in accordance with the fourth preferred embodiment of the present invention.

In FIG. 14, when the rod 4A is retracted from the barrel 21A, the flexible bracket 432A is moved backward from the front of the protrusion T, and the flexible bracket 432A has a length greater than the plane 434A, so that the flexible bracket 432A blocks the protrusion T and an end portion of the plane 434A to produce a one-way engagement effect, and the engagement section 43A can drive the needle seat 22A to displace, so as to achieve the same effect of the previous preferred embodiment.

In addition, the head holder section 221A of the needle seat 22A is abutted against the circular body 26A in the barrel 21A and warped by the barrel inverted hook plate 214A and blocked in the barrel 21A, so that when the rod 4A is pushed towards the barrel 21A, the head holder section 221A of the needle seat 22A can be positioned in the barrel 21A securely to assure that the seal ring 223A has the effect of preventing leakage.

What is claimed is:

1. A syringe with a blocking structure, comprising:
a cylindrical body including a flange adjacent a proximal end thereof, and a needle seat at an opposing distal end;
a rod;
a first one-way engagement unit including a circularly formed propping portion extending outwardly from the rod and a circularly formed flexible bracket extending outwardly from the rod and being in spaced overlaying relationship with respect to the propping portion, the flexible bracket having an external diameter greater than an external diameter of the propping portion and positioned intermediate to a pushing end of the rod and the propping portion; and
a second one-way engagement unit disposed distally of the first one-way engagement unit for engaging the needle seat when the rod is pushed to the distal end of the cylindrical body, thereby, when the rod is pushed backward with respect to the cylindrical body, proximity of the propping portion to the flexible bracket limits deformation of the flexible bracket upon contacting the flange to block the flexible bracket from moving past the flange, wherein the needle seat receives a needle thereon and the needle seat and the needle are pulled backward into the cylindrical body along with the rod.

2. The syringe with a blocking structure according to claim 1, wherein the flange is formed on an internal surface of the cylindrical body, characterized in that the rod comprises a rod body section, and an engagement section extended from the rod body section and accommodated in the needle seat, and the propping portion and the flexible bracket being extended outwardly from the rod body section.

3. The syringe with a blocking structure according to claim 1, wherein the needle seat includes a fitting section, and an additional flange is formed on an internal surface of the needle seat, characterized in that the rod comprises a rod body section, an engagement section extended from the rod body section and accommodated in the needle seat, and a top rod section extended from the engagement section and accommodated in the fitting section, and the propping portion and the flexible bracket are extended outwardly from the engagement section.

4. The syringe with a blocking structure according to claim 1, wherein the needle seat includes a fitting section, and an additional flange is formed on an internal surface of the fitting section, characterized in that the rod comprises a rod body section, an engagement section extended from the rod body section and accommodated in the needle seat, and a top rod section extended from the engagement section and accommodated in the fitting section, and the propping portion and the flexible bracket are extended outwardly from the top rod section.

5. The syringe with a blocking structure according to claim 1, wherein the needle seat includes a fitting section and two additional flanges, the three flanges being formed on internal surfaces of the cylindrical body, the needle seat, and the fitting section, respectively, characterized in that the syringe further comprises a third one-way engagement unit, and the rod comprises a rod body section, an engagement section extended from the rod body section and accommodated in the needle seat, and a top rod section extended from the engagement section and accommodated in the fitting section, wherein the second and the third one-way engagement units include corresponding second and third circularly formed propping portions and corresponding second and third flexible brackets, and the propping portions and the flexible brackets of the three one-way engagement units are extended from the rod body section respectively, and the engagement section and the top rod section are extended outwardly.

6. The syringe with a blocking structure according to claim 1, wherein the flange is disposed around the internal surface of the cylindrical body, wherein and the rod has an external diameter smaller than an internal diameter of the cylindrical body, and the propping portion has an external diameter equal to an internal diameter of the flange.

7. The syringe with a blocking structure according to claim 1, wherein the circular flexible bracket has a periphery formed by a plurality of hollow portions and serrated portions arranged alternately with one another.

8. The syringe with a blocking structure according to claim 1, wherein the flexible bracket has a perimeter portion deformable into an arcuate contour.

9. A syringe with a blocking structure, comprising:
a cylindrical body, including a barrel and a needle seat combined with the barrel, and a flange being formed at a middle position of an internal surface of the needle seat;
a rod, including a rod body section, an engagement section extended from the rod body section and accommodated in the needle seat, and a hollow cork cap covered onto the engagement section and plugged into the needle seat, wherein the engagement section has a circular groove, and a flexible bracket extends horizontally from the circular groove, and the flange has an internal diameter lesser than an external diameter of the flexible bracket, and the cork cap has a periphery with a thickness slightly smaller than a difference between the internal diameter of the flange and the external diameter of the flexible bracket, such that the periphery of the cork cap is protruded into the circular groove by the flange, and
the protrusion has an internal diameter smaller than the external diameter of the flexible bracket, and the circular groove has a bevel extended slantingly backward from a groove wall at a rear of the flexible bracket, and the circular groove has a plane extending horizontally from a groove wall at a front of the flexible bracket;
such that the cork cap together with the engagement section are pushed forward and plugged into the needle seat, and when the flexible bracket is moved forward from a rear of the protrusion, the flexible bracket is moved by the protrusion to tilt backward, so that the flexible bracket can pass through the protrusion, and after the flexible bracket passes through the protrusion, the flexible bracket restores its original horizontal position, and when the rod is refracted from the barrel, the flexible bracket is moved backward from a front of the protrusion, and the protrusion has an internal diameter smaller than the external diameter of the flexible bracket, so that the flexible bracket blocks the protrusion and an end position of the plane, and the engagement section drives the needle seat to displace.

10. A syringe with a blocking structure, comprising:
a barrel, having a through hole formed at a front end of the barrel, and a plurality of dovetail grooves uniformly formed at an end of the through hole and in the barrel, and each dovetail groove passing axially from the barrel into the end of the through hole,
and a barrel inverted hook plate disposed deeply into each dovetail groove in the barrel and at a position further than an internal side of the dovetail groove, and each barrel inverted hook plate being extended in a direction slightly downwardly towards the through hole and warped to an outside, and each barrel inverted hook plate having a dovetail member disposed at the end of the through hole and installed into the corresponding dovetail groove;
a circular body, with a square cross-section and a specific compressibility, and disposed in the barrel and at a bottom of the end of the through hole;
a needle seat, disposed at the end of the through hole of the barrel, and having a head holder section and a fitting section, and a periphery of the head holder section having a first circular portion and a second circular portion, and a circular groove being formed between the first circular portion and the second circular portion, and a front edge of the first circular portion abutting the circular body,
and when the barrel inverted hook plate is warped and extended into the circular groove and blocked by a rear edge of the first circular portion, a periphery of the second circular portion pushes away the barrel inverted hook plate and drives the dovetail member into the dovetail groove, and the head holder section at a rear edge of the second circular portion abuts a seal ring of the barrel, and the fitting section is extended from the head holder section to an exterior of the through hole;
and a rod, comprising a rod body section, an engagement section extending from the rod body section and accommodated in the needle seat, and a hollow cork cap covered onto the engagement section and plugged into the needle seat.

* * * * *